United States Patent [19]

Manzer et al.

[11] Patent Number: 5,243,106

[45] Date of Patent: Sep. 7, 1993

[54] PROCESSES USING ALUMINUM FLUORIDE CATALYST COMPOSITIONS FOR PREPARING 1,1-DICHLORO-1,2,2,2-TETRAFLUOROETHANE

[75] Inventors: Leo E. Manzer, Wilmington; Frederick N. Tebbe, Hockessin, both of Del.

[73] Assignee: E. I. Du Pont de Nemours and Company, Wilmington, Del.

[21] Appl. No.: 865,784

[22] Filed: Apr. 7, 1992

Related U.S. Application Data

[63] Continuation of Ser. No. 700,190, Jun. 3, 1991, abandoned.

[51] Int. Cl.⁵ .............................................. C07C 17/08
[52] U.S. Cl. ..................................................... 570/166
[58] Field of Search ........................................ 570/166

[56] References Cited

U.S. PATENT DOCUMENTS

| | | |
|---|---|---|
| 2,748,177 | 5/1956 | Miller et al. ............ 570/166 |
| 2,755,313 | 7/1956 | Calfee et al. . |
| 3,314,749 | 4/1967 | Fukui et al. . |
| 3,650,987 | 3/1972 | Vecchio et al. . |
| 3,720,722 | 3/1973 | Wada et al. ............ 510/166 |
| 4,605,798 | 8/1986 | Abel et al. . |
| 4,766,260 | 8/1988 | Manzer et al. . |
| 4,902,838 | 2/1990 | Manzer et al. . |
| 5,008,475 | 4/1991 | Manzer et al. . |

OTHER PUBLICATIONS

F. N. Tebbe, *J. Am. Ceram. Soc.*, 71 [4] pp. 204–206.
Chemical Abstracts 74:55778t.
Vecchio et al., *J. Fluorine Chem*, 4, pp. 117–139.

*Primary Examiner*—Alan Siegel

[57] ABSTRACT

A process is disclosed for transforming a saturated reactant (e.g. 1,1,2-trichloro-1,2,2-trifluoroethane) into a saturated product (e.g. 1,1-dichloro-1,2,2,2-tetrafluoroethane) by contacting a gaseous mixture comprising said reactant with an aluminum fluoride catalyst at an elevated temperature, which is characterized using a catalyst composition consisting essentially of an aluminum fluoride prepared by the reaction of aluminum hydroxide and HF. Also disclosed is a process for producing 2-chloro-1,1,1,2-tetrafluoroethane and/or 1,1,1,2-tetrafluoroethane by hydrodechlorinating 1,1-dichloro-1,2,2,2-tetrafluoroethane produced by said transformation.

20 Claims, No Drawings

PROCESSES USING ALUMINUM FLUORIDE CATALYST COMPOSITIONS FOR PREPARING 1,1-DICHLORO-1,2,2,2-TETRAFLUOROETHANE

This application is a continuation of application Ser. No. 07/700,190 filed Jun. 3, 1991, now abandoned.

FIELD OF THE INVENTION

This invention relates to catalysts and their use for the manufacture of haloethanes such as 1,1-dichloro-1,2,2,2-tetrafluoroethane (i.e. "CFC-114a"), and more particularly to the use of aluminum fluoride catalysts and use thereof for preparing haloethanes containing fluoride such as CFC-114a.

BACKGROUND OF THE INVENTION

Fluorinated aluminas are well known as fluorination or chlorofluorination catalysts. For example the use of both aluminum fluoride and aluminum fluoride containing iron, chromium and nickel for fluorination or chlorofluorination reactions is described in U.S. Pat. No. 3,650,987. The fluorided alumina is often prepared by the addition of HF to $Al_2O_3$. The products from these reactions contain large amounts of the symmetrical isomers of various chlorofluorocarbons. The addition of the metal dopants increases the amount of symmetrical isomers.

German (DDR) Patent Specification 117,580 discloses a process for the preparation of asymmetrical fluorochlorocarbon compounds of the $C_2$ series (e.g. CFC-114a) by the reaction of tetrachloroethylene, chlorine and hydrogen fluoride over a metal doped aluminum fluoride catalyst. In the example of this patent with the highest amount of asymmetrical products, the 1,1-dichloro-1,2,2,2-tetrafluoroethane (CFC-114a)/1,2-dichloro-1,1,2,2-tetra-fluoroethane (CFC-114) ratio is about 11.5; and the 1,1,1-trichloro-2,2,2-trifluoroethane (CFC-113a)/1,1,2-trichloro-1,2,2-trifluoroethane (CFC-113) ratio is about 8.0. However 57.4% of the product is chloropentafluoroethane (CFC-115), which is generally considered an undesirable byproduct in CFC-114a manufacturing processes. In another example where 6.1% of the product is CFC-115, the ratios of CFC-114a/CFC-114 and CFC-113a/CFC-113 are 7.3 and 3.8 respectively.

European Patent Application 317,981 discloses a process for isomerizing CFC-113 to CFC-113a followed by fluorination with HF to produce CFC-114a In the example of this patent with the highest ratio of CFC-114a/CFC-114 (52.7) the ratio of CFC-113a/CFC-113 is 1.1. In other examples the CFC-114a/CFC-114 ratio varied from 45.3 to 5.5 and the CFC-113a/CFC-113 ratio from 6.2 to 1.1.

Japanese Kokai 1-172347 discloses a process for the preparation of CFC-114a by first disproportionating CFC-114 to CFC-113a followed by reaction with HF. In the examples the CFC-114a/CFC-114 ratios vary from 9.0 to 16.7 and the CFC-113a/CFC-113 ratios from 0.1 to >36. In the high 113a/113 ratio example the yield of 114a is only 15.0%. In the other examples the yields of 114a varied from 43.0% to 51.0%.

It is also known in the art (GB 1,578,933) that both $CClF_2CClF_2$ (CFC-114) and $CF_3CCl_2F$ (CFC-114a) may be hydrogenated over a Pd catalyst to $CHF_2CHF_2$ (HFC-134) and $CF_3CH_2F$ (HFC-134a) respectively. The latter compound (HFC-134a) is considered a refrigerant for replacing $CCl_2F_2$ since it does not significantly contribute to stratospheric ozone depletion while $CCl_2F_2$ is suspected of being a major contributor. Other haloethanes containing fluoride are considered useful as refrigerants, blowing agents, solvents and/or as reagents for preparing such products.

Accordingly, there is continued interest in developing economic and efficient processes for preparing haloethanes containing fluoride such as 1,1-dichloro-1,2,2,2-tetrafluoroethane.

SUMMARY OF THE INVENTION

A process disclosed herein involves transforming a reactant having the formula $C_2H_xCl_yF_z$ wherein x is an integer from zero to 3, y is an integer from zero to 6, z is an integer from zero to 4, and the sum of x, y and z is 6, into a product which is different from said reactant and has the formula $C_2H_aCl_bF_d$ where a is an integer from zero to 3, b is an integer from zero to 5, d is an integer from 1 to 4, and the sum of a, b and d is 6, and where d is at least z. A process using aluminum fluoride catalysts is disclosed which comprises the step of contacting a gaseous mixture comprising the reactant and HF with a catalyst composition at an elevated temperature, wherein said catalyst composition consisting essentially of an aluminum fluoride prepared by the reaction of aluminum hydroxide and HF. In accordance with this invention, a process for transforming at least one compound selected from the group consisting of $CCl_3CCl_3$, $CCl_3CCl_2F$, $CCl_2FCCl_2F$, $CClF_2CCl_3$, and $CCl_2FCClF_2$ into 1,1-dichloro-1,2,2,2-tetrafluoroethane by contacting a gaseous mixture comprising said at least one compound HF and with an aluminum fluoride catalyst at an elevated temperature is provided, which is characterized by using a catalyst composition consisting essentially of an aluminum fluoride prepared by the reaction of aluminum hydroxide with HF. The 1,1-dichloro-1,2,2,2-tetrafluoroethane prepared by the process may be hydrodechlorinated to produce 2-chloro-1,1,1,2-tetrafluoroethane and/or tetrafluoroethane.

DETAILED DESCRIPTION OF THE INVENTION

A saturated reactant having the formula $C_2H_xCl_yF_z$ wherein x is an integer from zero to 3, y is an integer from zero to 6, z is an integer from zero to 4, and the sum of x, y and z is 6, may be transformed into a saturated product which is different from said reactant and has the formula $C_2H_aCl_bF_d$ where a is an integer from zero to 3, b is an integer from zero to 5, d is an integer from 1 to 4, and the sum of a, b and d is 6, and where d is at least z by using aluminum fluoride catalysts. The transformations involved in these processes can include various types of conversion reactions such as fluorination, chlorofluorination, isomerization, disproportionation, and combinations of such reactions. One technique for transforming a reactant to a product comprises the step of contacting a gaseous mixture comprising HF with a catalyst composition at an elevated temperature, wherein said catalyst composition consists essentially of an aluminum fluoride prepared by the reaction of aluminum hydroxide and HF. For example, a process for isomerizing saturated $C_2$ fluorohydrocarbons having lesser thermodynamic stability to fluorohydrocarbons having greater thermodynamic stability can be accomplished by contacting in the gaseous phase at a temperature from about 200° C. to about 475° C. at least one $C_2$ saturated fluorocarbon with a catalyst composition of this type. We have found $CCl_3CCl_3$, $CCl_3CCl_2F$, $CCl_2FCCl_2F$, $CClF_2CCl_3$, and $CCl_2FCClF_2$ are preferred reactants for such a technique. Indeed a process for transforming at least one compound selected from the group consisting of $CCl_3CCl_3$, $CCl_3CCl_2F$, $CCl_2FCCl_2F$, $CClF_2CCl_3$, and $CCl_2FCClF_2$ into 1,1-dichloro-1,2,2,2-tetrafluoroethane by contacting a gaseous mixture comprising HF and said at least one compound with an aluminum fluoride catalyst at an elevated temperature is provided in accordance with this invention, and is characterized by using a catalyst composition consisting essentially of an aluminum fluoride prepared by the reaction of aluminum hydroxide and HF. The most preferred reactant for this process is 1,1,2-trichloro-1,2,2-trifluoroethane.

The interaction of the reactant with HF and optionally $Cl_2$ in the presence of the catalyst composition of the instant invention is conducted at an elevated temperature. Suitable temperatures are generally within the range of about 200° C. to 475° C. Preferably the temperature is within the range of about 300° C. to 400° C. and most preferably is within the range of about 350° C. to 375° C. Contact times can influence the yield of the reaction to some extent. Preferably the temperature and contact time are balanced to achieve a desirable yield. For example, in the process of this invention where CFC-113 is transformed into CFC-114a, the temperature and contact time are preferably controlled to achieve the desired product yield (e.g. at least about 95% total of CFC-114a and recyclable by-products). Preferably the aluminum fluoride purity of the catalyst composition is sufficient to provide a molar ratio of 1,1-dichloro-1,2,2,2-tetrafluoroethane to 1,2-dichloro-1,1,2,2-tetrafluoroethane (i.e. CFC-114a to CFC-114)of at least about 45 and most preferably sufficient to provide a molar ratio of CFC-114a to CFC-114 of at least about 47.5. A contact time within the range of about 5 to 100 seconds is typical. Preferably the contact time is within the range of about 10 to 90 seconds, and most preferably is within the range of about 15 to 60 seconds.

The HF in the gaseous mixture is preferably at least the stoichiometric amount needed to produce the product (e.g. CFC-114a). The molar ratio of the HF to the is typically within the range of about 1:1 to 20:1. In the process of this invention where CFC-113 is transformed into CFC-114a, the ratio of HF to CFC-113 is preferably within the range of about 1:1 to 10:1, and is most preferably within the range of about 1:1 to 3:1.

Typically $Cl_2$ is not needed to produce the product. However it can nevertheless be optionally added to facilitate the reaction. For example, in the process of this invention where CFC-113 is transformed into CFC-114a, the gaseous mixture may optionally comprise $Cl_2$; and the molar ratio of $Cl_2$ when present, to the reactant CFC-113 is preferably within the range of about 0.01:1 to 2:1, and most preferably is about 1:1.

Products such as CFC-114a can be separated by a usual method such as fractional distillation. By-products having no more fluorine atoms per molecule than the desired product are considered recyclable, and may advantageously be further contacted with the catalyst composition used in this invention. Thus, for CFC-114a production, by-products such as $C_2Cl_5F$, $C_2Cl_4F_2$, $C_2F_3Cl_3$ and $CClF_2CClF_2$ are considered recyclable.

The reaction of the reactant with HF (and, optionally chlorine) may be conducted in any suitable reactor, including fixed and fluidized bed reactors which are charged with the catalyst compositions. The reaction vessel should be constructed from materials which are resistant to the corrosive effects of HF and $Cl_2$ such as Hastelloy ® nickel alloy and Inconel ® nickel alloy. Optionally, before the catalyst is contacted by the reactant, it may be pretreated with gaseous HF.

Pressure is not critical. Atmospheric and superatmospheric pressures are the most convenient and are therefore preferred.

1,1-dichloro-1,2,2,2-tetrafluoroethane produced by this invention has utility as a solvent and as an intermediate for the preparation of 2-chloro-1,1,1,2-tetrafluoroethane and/or 1,1,1,2-tetrafluoroethane. Indeed an improved process for producing 1,1,1,2-tetrafluoroethane and/or 2-chloro-1,1,2,2-tetrafluoroethane by hydrodechlorinating 1,1-dichloro-1,2,2,2-tetrafluoroethane is provided in accordance with this invention. The improvement comprises the step of preparing CFC-114a by using the reactant 1,1,2-trichloro-1,2,2-trifluoroethane and the catalyst compositions of this invention as described above.

The catalyst compositions used in accordance with this invention consist essentially of an aluminum fluoride prepared by the reaction of aluminum hydroxide with HF.

The catalyst composition of this invention may be suitably prepared by reacting aqueous HF e.g. 48% solution) with aluminum hydroxide. Suitable aluminum hydroxide may be prepared by the hydrolysis of $AlR_3$, where each R is independently selected from $C_1$ to $C_6$ alkyl groups. For example, a preparation of high purity $Al(OH)_3$ prepared by the hydrolysis of $Al(CH_2CH_3)_3$ is described by F. N. Tebbe et al., *J. Am. Ceram. Soc.*, 71 [4], C-204 - C-206, (1988). Suitable aluminum hydroxide may also be prepared by hydrolysis of $Al(OR)_3$, where each R is independently selected from $C_1$ to $C_6$ alkyl groups. For example, high purity $Al(OH)_3$ may be prepared by the hydrolysis of $Al(OCH(CH_3)CH_2CH_3)_3$.

A particularly useful catalyst composition consisting essentially of an aluminum fluoride is prepared by dissolving aluminum hydroxide in aqueous HF; evaporating the resulting solution to obtain a residue of an aluminum fluoride; and heating said residue to produce a dried solid. The catalyst compositions of this invention are also useful for catalyzing other reactions such as the chlorofluorination of $CF_3CCl_3$, $CF_3CHClF$ and/or $CF_3CH_3$ to CFC-114a, isomerization of $CClF_2$-$CClF_2$ to $CCl_2F$-$CF_3$, isomerization of $CHF_2$-$CHF_2$ to $CH_2F$-$CF_3$, fluorination of $CF_3$-$CHCl_2$ to $CF_3$-$CHClF$ and fluorination of $CHCl=CCl_2$ to $CClF_2CH2Cl$ and $CF_3CH2Cl$.

Practice of the invention will become further apparent from the following non-limiting examples.

EXAMPLE I

Aluminum sec-butoxide (Alfa, 95%), about 300 g, was placed in an open dish and allowed to hydrolyze in air over two days. The aluminum hydroxide produced was a powder and clusters of powdery solids. In a polyethylene tray a portion of the aluminum hydroxide (39 g) was dissolved in 48% aqueous hydrofluoric acid (100 mL). The volatiles were evaporated at ambient temperature over three days in a fume hood. The resulting white residue was dried at 110° C. for 48 hours. The solid was then heated in air at a rate of 5° C./min to 500° C., and held at this temperature for three hours. After cooling, the solid (30.3 g) was crushed and passed through a sieve to yield fines (12.8 g and a fraction of granules 12×20 mesh in size (17.5 g). Analysis showed 31.5% Al and 227 ppm (0.0227%) of metal ion impurities.

EXAMPLE II

A reactor (a 0.5 inch ID, 12 inch long Inconel® nickel alloy pipe) was charged with aluminum fluoride 15.7 g, 25 mL) prepared as described in Example I, and placed in a sand bath. The bath was gradually heated to 250° C. while nitrogen gas at a flow rate of 50cc/minute was passed through the reactor to remove traces of water. HF and nitrogen gas (1:4 molar ratio) were then passed through the reactor. An exotherm of about 10° C., which travelled down the reactor, was observed. The temperature was gradually raised to 450° C., the nitrogen flow decreased with time until neat HF was passed through the reactor. The HF flow was stopped after no further exotherm was recorded. $HF/CCl_2FCClF_2/Cl_2$ in a 5/1/1 molar ratio was then passed over the catalyst at 375° C. and a 15 second contact time. The reactor effluent was sampled on-line with a Hewlett-Packard 5890 gas chromatograph using a 20 foot long, ⅛" diameter, column containing Krytox ® perfluorinated polyether on an inert support and a helium flow of 35 cc/minute. Gas chromatographic conditions were 70° C. for 3 minutes followed by temperature programming to 180° C. at a rate of 6° C./minute. Analysis showed the following to be present (area percent : 0.1% $CCl_2FCCl_2F/CClF_2CCl_3$, 3.8% $CCl_2FCClF_2$ (CFC-113), 10.7% $CF_3CCl_3$ (CFC-113a), 1.8% $CClF_2CClF_2$ (CFC-114), 83.3% $CF_3CCl_2F$ (CFC-114a), and 0.5% $CClF_2CF_3$ (CFC-115).

The yield to useful products is greater than 99% and the molar ratio of CFC-114a/CFC-114 is 46.

EXAMPLE III

After the run of Example II above, $HF/CCl_2FCClF_2$ in a 5/1 molar ratio was then passed through the reactor and over the catalyst at 400° C. and a 17 second contact time. The reactor effluent was sampled on-line with a Hewlett-Packard 5890 gas chromatograph using a 20 foot long, ⅛" diameter, column containing Krytox ® perfluorinated polyether on an inert support and a helium flow of 35 cc/minute. Gas chromatographic conditions were 70° C. for 3 minutes followed by temperature programming to 180° C. at a rate of 6° C./minute. Analysis showed the following to be present area percent): 0.1% $CCl_2FCClF_2$ (CFC-113), 1.4% $CF_3CCl_3$ (CFC-113a), 5.9% $CClF_2CClF_2$ (CFC-114), 89.6% $CF_3CCl_2F$ (CFC-114a), and 3.1% $CClF_2CF_3$ (CFC-115).

The yield to useful products is greater than 96% and the molar ratio of CFC-114a/CFC-114 is 15.

Particular embodiments of the invention are described in the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

We claim:

1. A process for transforming at least one compound selected from the group consisting of $CCl_3CCl_3$, $CCl_3CCl_2F$, $CCl_2FCCl_2F$, $CClF_2CCl_3$, and $CCl_2FCClF_2$ into 1,1-dichloro-1,2,2,2-tetrafluoroethane by contacting a gaseous mixture comprising HF and said at least one compound with an aluminum fluoride catalyst at an elevated temperature, characterized by using a catalyst composition consisting essentially of an aluminum fluoride which is (i) of sufficient purity to provide a molar ratio of 1,1-dichloro-1,2,2,2-tetrafluoroethane to 1,2-dichloro-1,1,2,2-tetrafluoroethane of 14 to 46, and (ii) the product of the reaction of HF and high purity aluminum hydroxide prepared by the hydrolysis of $AlR_3$ or the hydrolysis of $AlOR_3$ where each R is selected from $C_1$ to $C_6$ alkyl groups.

2. The process of claim 1 wherein by-products having less than five fluorine atoms per molecule are recycled.

3. The process of claim 1 wherein the molar ratio of said HF to said at least one compound is within the range of about 1:1 to 20:1.

4. A process for transforming at least one compound selected from the group consisting of $CCl_3CCl_3$, $CCl_3CCl_2F$, $CCl_2FCCl_2F$, $CClF_2CCl_3$, and $CCl_2FCClF_2$ into 1,1-dichloro-1,2,2,2-tetrafluoroethane by contacting a gaseous mixture comprising HF and said at least one compound with an aluminum fluoride catalyst at an elevated temperature, characterized by (a) using a catalyst composition consisting essentially of an aluminum fluoride having 0.0227 weight percent metal ion impurities prepared by the reaction of HF and aluminum hydroxide, and (b) contacting a gaseous mixture comprising HF, said at least one compound and $Cl_2$ with the catalyst.

5. The process of claim 4 wherein the molar ratio of said $Cl_2$ to said at least one compound is within the range of about 0.01:1 to 2:1.

6. The process of claim 1 wherein the at least one compound is 1,1,2-trichloro-1,2,2-trifluoroethane.

7. The process of claim 1 wherein before the catalyst is contacted by said at least one compound is pretreated with HF gas.

8. The process of claim 1 wherein said aluminum hydroxide is prepared by the hydrolysis of $Al(OR)_3$ where each R is independently selected from $C_1$ to $C_6$ alkyl groups.

9. The process of claim 1 wherein the temperature is within the range of about 200° C. to 475° C.

10. An improved process for producing 2-chloro-1,1,1,2-tetrafluoroethane and/or 1,1,1,2-tetrafluoroethane by hydrodechlorinating 1,1-dichloro-1,2,2,2-tetrafluoroethane, the improvement comprising the step of preparing said 1,1-dichloro-1,2,2,2-tetrafluoroethane by contacting a gaseous mixture comprising 1,1,2-trichloro-1,2,2-trifluoroethane and HF with a catalyst composition at a temperature within the range of about 200° C. to 475° C., said catalyst composition consisting essentially of an aluminum fluoride which is (i) of sufficient purity to provide a molar ratio of 1,1-dichloro-1,2,2,2-tetrafluoroethane to 1,2-dichloro-1,1,2,2-tetrafluoroethane of from 15 to 46, and (ii) the product of the reaction of HF and aluminum hydroxide prepared by the hydrolysis of $AlR_3$ or the hydrolysis of $AlOR_3$ where each R is selected from $C_1$ to $C_6$ alkyl groups.

11. The process of claim 1 wherein the gaseous mixture further comprises $Cl_2$.

12. The process of claim 11 wherein the molar ratio of said $Cl_2$ to said at least one compound is within the range of about 0.01:1 to 2:1.

13. The process of claim 12 wherein the aluminum fluoride has 0.0227 weight percent metal ion impurities.

14. The process of claim 11 characterized by using a catalyst composition consisting essentially of aluminum fluoride which is of sufficient purity to provide a molar ratio of 1,1-dichloro-1,2,2,2-tetrafluoroethane to 1,2-dichloro-1,1,2,2-tetrafluoroethane of 46.

15. The process of claim 14 wherein the molar ratio of said $Cl_2$ to said at least one compound is within the range of about 0.01:1 to 2:1.

16. The process of claim 1 wherein the aluminum fluoride has 0.0227 weight percent metal ion impurities.

17. The improved process of claim 10 wherein the aluminum fluoride has 0.0227 weight percent metal ion impurities.

18. The improved process of claim 10 wherein the improvement is characterized by said gaseous mixture comprising $Cl_2$, and by using a catalyst composition consisting essentially of aluminum fluoride which is of sufficient purity to provide a molar ratio of 1,1-dichloro-1,2,2,2-tetrafluoroethane to 1,2-dichloro-1,1,2,2-tetrafluoroethane of 45 to 46.

19. The improved process of claim 18 wherein the molar ratio of said $Cl_2$ to said at least one compound is within the range of about 0.01:1 to 2:1.

20. The improved process of claim 19 wherein the aluminum fluoride has 0.0227 weight percent metal ion impurities.

* * * * *